US009852271B2

(12) United States Patent
Aragones et al.

(10) Patent No.: US 9,852,271 B2
(45) Date of Patent: Dec. 26, 2017

(54) PROCESSING DATA OF A USER PERFORMING AN ATHLETIC ACTIVITY TO ESTIMATE ENERGY EXPENDITURE

(75) Inventors: Tesa Aragones, Portland, OR (US); Adriana Guerrero, Beaverton, OR (US); Steve Holmes, Beaverton, OR (US); Christina S. Self, Portland, OR (US); Aaron B. Weast, Portland, OR (US); Paul T. Winsper, Beaverton, OR (US); Jay C. Blahnik, Laguna Beach, CA (US)

(73) Assignee: NIKE, Inc., Beaverton, OR (US)

( * ) Notice: Subject to any disclaimer, the term of this patent is extended or adjusted under 35 U.S.C. 154(b) by 522 days.

(21) Appl. No.: 13/324,812

(22) Filed: Dec. 13, 2011

(65) Prior Publication Data
US 2012/0268592 A1   Oct. 25, 2012

Related U.S. Application Data

(63) Continuation-in-part of application No. 13/290,359, filed on Nov. 7, 2011, and a continuation-in-part of
(Continued)

(51) Int. Cl.
*G06F 19/00* (2011.01)
*A61B 5/16* (2006.01)
(Continued)

(52) U.S. Cl.
CPC ............ *G06F 19/3481* (2013.01); *A61B 5/02* (2013.01); *A61B 5/103* (2013.01); *A61B 5/16* (2013.01);
(Continued)

(58) Field of Classification Search
CPC .. A61B 5/02; A61B 5/103; A61B 5/16; A61B 5/18; A61B 15/02; A61B 21/0053;
(Continued)

(56) References Cited

U.S. PATENT DOCUMENTS 3,145,484 A    8/1964  Bayley
5,184,295 A    2/1993  Mann
(Continued)

FOREIGN PATENT DOCUMENTS

CN   103493056 A   1/2014
DE   29720110      1/1998
(Continued)

OTHER PUBLICATIONS

United States Patent and Trademark Office, "Final Office Action," issued in connection with U.S. Appl. No. 13/304,064, mailed Oct. 24, 2013, 13 pages.
(Continued)

*Primary Examiner* — Nikolai A Gishnock
(74) *Attorney, Agent, or Firm* — Banner & Witcoff, Ltd.

(57) ABSTRACT

Example embodiments may relate to a system, method, apparatus, and computer readable media configured for prompting a user to perform an exercise, monitoring form of the user while performing the exercise, and calculating an energy expenditure estimate for the user performing the exercise based on a type of the exercise and on the form of the user.

20 Claims, 12 Drawing Sheets

Related U.S. Application Data application No. 13/304,064, filed on Nov. 23, 2011, and a continuation-in-part of application No. 13/304,056, filed on Nov. 23, 2011.

(60) Provisional application No. 61/422,511, filed on Dec. 13, 2010, provisional application No. 61/432,472, filed on Jan. 13, 2011, provisional application No. 61/433,792, filed on Jan. 18, 2011.

(51) Int. Cl.

| | | |
|---|---|---|
| G09B 19/00 | (2006.01) | |
| A61B 5/103 | (2006.01) | |
| G02B 27/14 | (2006.01) | |
| A61B 5/02 | (2006.01) | |
| A63B 5/16 | (2006.01) | |
| A63B 21/005 | (2006.01) | |
| A63B 5/08 | (2006.01) | |
| A63B 24/00 | (2006.01) | |
| A63B 69/00 | (2006.01) | |
| A63B 21/00 | (2006.01) | |
| A63B 69/36 | (2006.01) | |
| A63B 71/06 | (2006.01) | |

(52) U.S. Cl.
CPC .................. *A63B 5/08* (2013.01); *A63B 5/16* (2013.01); *A63B 21/0053* (2013.01); *A63B 21/0058* (2013.01); *A63B 21/153* (2013.01); *A63B 24/00* (2013.01); *A63B 24/0006* (2013.01); *A63B 24/0062* (2013.01); *A63B 69/00* (2013.01); *A63B 69/36* (2013.01); *A63B 71/0622* (2013.01); *G02B 27/14* (2013.01); *G06F 19/00* (2013.01); *G09B 19/0038* (2013.01); *G09B 19/0076* (2013.01); *A63B 2024/0012* (2013.01); *A63B 2208/12* (2013.01)

(58) Field of Classification Search
CPC ....... A61B 21/0058; A63B 15/02; A63B 5/16; A63B 5/18; A63B 21/0053; A63B 21/0058; A63B 21/153; A63B 22/02; A63B 22/08; A63B 22/023; A63B 24/00; A63B 24/003; A63B 24/0006; A63B 24/0062; A63B 69/00; A63B 69/36; A63B 71/0062; A63B 2208/12; A63B 2208/16; A63B 2208/51; A63B 2208/80; A63B 2021/0012; A63B 2021/0026; G02B 27/14; G09B 19/00; G09B 19/0038; G09B 19/0076; G06F 19/3481
USPC ......... 434/247; 482/4–8; 600/481, 500, 503, 600/595; 359/629, 630
See application file for complete search history.

(56) References Cited

U.S. PATENT DOCUMENTS

| | | | |
|---|---|---|---|
| 5,277,197 A * | 1/1994 | Church et al. ............... 600/546 |
| 5,288,078 A * | 2/1994 | Capper et al. ................. 463/39 |
| 5,335,188 A * | 8/1994 | Brisson ........................ 702/163 |
| 5,511,789 A | 4/1996 | Nakamura |
| 5,524,637 A | 6/1996 | Erickson |
| 5,527,239 A | 6/1996 | Abbondanza |
| 5,598,849 A * | 2/1997 | Browne ........................ 600/520 |
| 5,655,316 A | 8/1997 | Huang |
| 5,667,459 A * | 9/1997 | Su ..................................... 482/4 |
| 5,688,137 A | 11/1997 | Bustance |
| 5,791,351 A | 8/1998 | Curchod |
| 5,826,578 A | 10/1998 | Curchod |
| 5,836,770 A | 11/1998 | Powers |
| 5,846,086 A * | 12/1998 | Bizzi et al. ................... 434/247 |
| 5,904,484 A | 5/1999 | Burns |
| 5,913,727 A * | 6/1999 | Ahdoot ........................... 463/39 |
| 5,955,957 A | 9/1999 | Calabrese et al. |
| 5,976,083 A | 11/1999 | Richardson et al. |
| 6,126,449 A | 10/2000 | Burns |
| 6,308,565 B1 | 10/2001 | French et al. |
| 6,316,934 B1 * | 11/2001 | Amorai-Moriya et al. ........................ 324/207.17 |
| 6,416,327 B1 | 7/2002 | Wittenbecher |
| 6,428,449 B1 * | 8/2002 | Apseloff ............................ 482/3 |
| 6,516,222 B2 * | 2/2003 | Fukuda ........................ 600/547 |
| 6,663,491 B2 | 12/2003 | Watabe et al. |
| 6,743,167 B2 * | 6/2004 | Balkin et al. ................. 600/137 |
| 6,765,726 B2 * | 7/2004 | French et al. ................ 359/630 |
| 6,788,200 B1 | 9/2004 | Jamel et al. |
| 6,834,436 B2 | 12/2004 | Townsend et al. |
| 6,836,744 B1 * | 12/2004 | Asphahani et al. .......... 702/141 |
| 6,876,496 B2 * | 4/2005 | French et al. ................ 359/630 |
| 7,018,211 B1 | 3/2006 | Birkholzer et al. |
| 7,079,889 B2 * | 7/2006 | Nakada ........................ 600/547 |
| 7,163,490 B2 * | 1/2007 | Chen ................................. 482/8 |
| 7,192,401 B2 * | 3/2007 | Saalasti et al. .............. 600/500 |
| 7,254,516 B2 * | 8/2007 | Case et al. ................... 702/182 |
| 7,265,666 B2 | 9/2007 | Daniel |
| 7,433,805 B2 * | 10/2008 | Vock ...................... A42B 3/046 702/188 |
| 7,442,131 B2 | 10/2008 | Milana |
| 7,493,232 B1 * | 2/2009 | Surina ........................... 702/160 |
| 7,497,807 B2 | 3/2009 | Neff et al. |
| 7,497,812 B2 | 3/2009 | Neff et al. |
| 7,556,590 B2 | 7/2009 | Watterson et al. |
| 7,628,730 B1 | 12/2009 | Watterson et al. |
| 7,717,858 B2 | 5/2010 | Massad |
| 7,736,272 B2 * | 6/2010 | Martens ................. A63B 22/00 482/1 |
| 7,771,293 B1 | 8/2010 | Vann |
| 7,771,320 B2 | 8/2010 | Riley et al. |
| 7,782,358 B2 | 8/2010 | Nieminen et al. |
| 7,783,347 B2 | 8/2010 | Abourizk et al. |
| 7,789,800 B1 | 9/2010 | Watterson et al. |
| 7,846,067 B2 | 12/2010 | Hanoun |
| 7,846,069 B2 * | 12/2010 | Martens ................. A63B 22/00 482/1 |
| 7,857,708 B2 | 12/2010 | Ueda et al. |
| 7,894,849 B2 | 2/2011 | Kass et al. |
| 7,927,253 B2 | 4/2011 | Vincent et al. |
| 7,967,728 B2 | 6/2011 | Zavadsky et al. |
| 7,978,217 B2 | 7/2011 | Camhi |
| 7,985,164 B2 | 7/2011 | Ashby |
| 8,012,064 B2 * | 9/2011 | Martens ................. A63B 22/00 482/1 |
| 8,029,411 B2 | 10/2011 | Johnson |
| 8,038,549 B2 | 10/2011 | Vann |
| 8,038,578 B2 | 10/2011 | Olrik et al. |
| 8,118,710 B2 * | 2/2012 | Weinman et al. ................. 482/2 |
| 8,230,367 B2 * | 7/2012 | Bell et al. .................... 715/863 |
| 8,235,870 B2 | 8/2012 | Hamilton |
| 8,284,157 B2 * | 10/2012 | Markovic et al. ........... 345/156 |
| 8,284,847 B2 * | 10/2012 | Adermann ............... 375/240.29 |
| 8,409,057 B2 * | 4/2013 | Martens ................. A63B 22/00 482/1 |
| 8,435,177 B2 * | 5/2013 | Lanfermann ....... A63B 24/0006 434/247 |
| 8,460,199 B2 * | 6/2013 | Rulkov et al. ............... 600/503 |
| 8,465,108 B2 | 6/2013 | Markovic et al. |
| 8,503,086 B2 | 8/2013 | French et al. |
| 8,523,667 B2 | 9/2013 | Clavin et al. |
| 8,568,277 B2 | 10/2013 | Johnson |
| 8,568,330 B2 * | 10/2013 | Mollicone et al. ........... 600/508 |
| 8,589,114 B2 | 11/2013 | Papadourakis |
| 8,602,988 B2 | 12/2013 | Hunt et al. |
| 8,616,989 B2 | 12/2013 | Bentley |
| 8,676,541 B2 * | 3/2014 | Schrock .................... A43B 3/00 702/188 |
| 8,702,485 B2 | 4/2014 | Flury et al. |
| 8,758,201 B2 | 6/2014 | Ashby et al. |
| 8,784,270 B2 | 7/2014 | Ashby et al. |
| 8,784,307 B1 | 7/2014 | Groteke et al. |

(56) References Cited

U.S. PATENT DOCUMENTS

| | | | |
|---|---|---|---|
| 8,812,428 B2* | 8/2014 | Mollicone et al. | 706/52 |
| 8,854,304 B2 | 10/2014 | Nishimoto et al. | |
| 8,858,400 B2 | 10/2014 | Johnson | |
| 8,861,091 B2* | 10/2014 | French et al. | 359/630 |
| 8,892,219 B2 | 11/2014 | Pryor | |
| 9,008,973 B2* | 4/2015 | French | 702/19 |
| 9,078,585 B2 | 7/2015 | Miyazaki et al. | |
| 9,141,759 B2 | 9/2015 | Burich et al. | |
| 9,154,739 B1 | 10/2015 | Nicolaou et al. | |
| 9,317,660 B2 | 4/2016 | Burich et al. | |
| 9,545,541 B2* | 1/2017 | Aragones | A61B 5/74 |
| 9,630,059 B2 | 4/2017 | Burich et al. | |
| 2002/0019258 A1* | 2/2002 | Kim et al. | 463/36 |
| 2003/0040348 A1* | 2/2003 | Martens | A63B 24/0087 463/1 |
| 2003/0054327 A1* | 3/2003 | Evensen | 434/252 |
| 2004/0087366 A1* | 5/2004 | Shum et al. | 463/36 |
| 2004/0102931 A1 | 5/2004 | Ellis et al. | |
| 2004/0112151 A1 | 6/2004 | Maxwell et al. | |
| 2004/0162194 A1* | 8/2004 | Habing | 482/99 |
| 2005/0079905 A1* | 4/2005 | Martens | 463/1 |
| 2005/0085348 A1* | 4/2005 | Kiefer et al. | 482/72 |
| 2005/0101887 A1 | 5/2005 | Stark et al. | |
| 2005/0113650 A1 | 5/2005 | Pacione et al. | |
| 2005/0113652 A1 | 5/2005 | Stark et al. | |
| 2005/0196737 A1 | 9/2005 | Mann | |
| 2005/0209050 A1 | 9/2005 | Bartels | |
| 2005/0239026 A1 | 10/2005 | Suzuki et al. | |
| 2005/0272517 A1 | 12/2005 | Funk et al. | |
| 2006/0025282 A1* | 2/2006 | Redmann | A61B 5/103 482/8 |
| 2006/0040793 A1* | 2/2006 | Martens | A63B 22/00 482/8 |
| 2006/0079800 A1* | 4/2006 | Martikka | A61B 5/0488 600/546 |
| 2006/0136173 A1 | 6/2006 | Case et al. | |
| 2006/0166737 A1 | 7/2006 | Bentley | |
| 2006/0205569 A1 | 9/2006 | Watterson et al. | |
| 2006/0229170 A1 | 10/2006 | Ozawa et al. | |
| 2006/0247070 A1* | 11/2006 | Funk et al. | 473/222 |
| 2007/0050715 A1 | 3/2007 | Behar | |
| 2007/0118406 A1 | 5/2007 | Killin et al. | |
| 2007/0155588 A1 | 7/2007 | Stark et al. | |
| 2007/0177024 A1 | 8/2007 | Camhi | |
| 2007/0213178 A1 | 9/2007 | Lemmela | |
| 2007/0232453 A1* | 10/2007 | Hanoun | 482/7 |
| 2007/0270214 A1 | 11/2007 | Bentley | |
| 2007/0271065 A1 | 11/2007 | Gupta et al. | |
| 2007/0272011 A1 | 11/2007 | Chapa et al. | |
| 2008/0096726 A1 | 4/2008 | Riley et al. | |
| 2008/0161733 A1 | 7/2008 | Einav et al. | |
| 2008/0189291 A1 | 8/2008 | Hsu | |
| 2008/0200312 A1 | 8/2008 | Tagliabue | |
| 2008/0212032 A1 | 9/2008 | Seiller et al. | |
| 2008/0254866 A1 | 10/2008 | Young et al. | |
| 2008/0281550 A1 | 11/2008 | Hogle et al. | |
| 2009/0042695 A1 | 2/2009 | Chien et al. | |
| 2009/0044429 A1 | 2/2009 | Cook et al. | |
| 2009/0149299 A1 | 6/2009 | Tchao et al. | |
| 2009/0171614 A1 | 7/2009 | Damen | |
| 2009/0269728 A1 | 10/2009 | Verstegen et al. | |
| 2009/0298650 A1* | 12/2009 | Kutliroff | 482/8 |
| 2009/0299232 A1 | 12/2009 | Lanfermann et al. | |
| 2010/0056340 A1 | 3/2010 | Ellis et al. | |
| 2010/0063778 A1* | 3/2010 | Schrock et al. | 702/188 |
| 2010/0125026 A1 | 5/2010 | Zavadski et al. | |
| 2010/0125028 A1 | 5/2010 | Heppert | |
| 2010/0137748 A1 | 6/2010 | Sone et al. | |
| 2010/0144414 A1* | 6/2010 | Edis et al. | 463/8 |
| 2010/0197462 A1 | 8/2010 | Piane, Jr. | |
| 2010/0210359 A1 | 8/2010 | Krzeslo et al. | |
| 2010/0210975 A1 | 8/2010 | Anthony, III et al. | |
| 2010/0217738 A1 | 8/2010 | Sarel | |
| 2010/0227302 A1 | 9/2010 | McGilvery et al. | |
| 2010/0234184 A1* | 9/2010 | Le Page et al. | 482/8 |
| 2010/0248901 A1* | 9/2010 | Martens | A63B 22/00 482/8 |
| 2010/0302142 A1* | 12/2010 | French et al. | 345/156 |
| 2010/0316983 A1 | 12/2010 | Johns, Jr. | |
| 2010/0332243 A1 | 12/2010 | Weigman et al. | |
| 2011/0077129 A1* | 3/2011 | Martens | A63B 22/00 482/8 |
| 2011/0111922 A1 | 5/2011 | Weinman et al. | |
| 2011/0111924 A1* | 5/2011 | Jones et al. | 482/8 |
| 2011/0112771 A1 | 5/2011 | French | |
| 2011/0131005 A1* | 6/2011 | Ueshima | A63B 24/0062 702/141 |
| 2011/0136627 A1* | 6/2011 | Williams | 482/8 |
| 2011/0158912 A1 | 6/2011 | Wright et al. | |
| 2011/0212791 A1 | 9/2011 | Ueda et al. | |
| 2011/0224557 A1 | 9/2011 | Banet et al. | |
| 2011/0229864 A1 | 9/2011 | Short et al. | |
| 2011/0251021 A1 | 10/2011 | Zavadsky et al. | |
| 2011/0270135 A1* | 11/2011 | Dooley et al. | 600/595 |
| 2011/0275907 A1 | 11/2011 | Inciardi et al. | |
| 2011/0306491 A1 | 12/2011 | Belisle | |
| 2011/0307821 A1* | 12/2011 | Martens | A63B 22/00 715/772 |
| 2012/0034971 A1 | 2/2012 | Harp et al. | |
| 2012/0038627 A1 | 2/2012 | Sung et al. | |
| 2012/0130886 A1 | 5/2012 | Shergill et al. | |
| 2012/0143358 A1 | 6/2012 | Adams et al. | |
| 2012/0234111 A1 | 9/2012 | Molyneux et al. | |
| 2012/0271143 A1 | 10/2012 | Aragones et al. | |
| 2012/0315986 A1* | 12/2012 | Walling | 463/31 |
| 2012/0315987 A1* | 12/2012 | Walling | 463/31 |
| 2013/0019694 A1 | 1/2013 | Molyneux et al. | |
| 2013/0022947 A1* | 1/2013 | Muniz Simas | G09B 19/00 434/236 |
| 2013/0022950 A1* | 1/2013 | Muniz Simas | G09B 7/02 434/238 |
| 2013/0108993 A1* | 5/2013 | Katz | 434/127 |
| 2013/0281796 A1* | 10/2013 | Pan | A61B 5/7435 600/301 |
| 2013/0295539 A1 | 11/2013 | Wilson et al. | |
| 2013/0338802 A1* | 12/2013 | Winsper et al. | 700/92 |
| 2014/0073486 A1 | 3/2014 | Ahmed et al. | |

FOREIGN PATENT DOCUMENTS

| | | |
|---|---|---|
| GB | 2415788 | 1/2006 |
| JP | H8-57093 A | 3/1996 |
| JP | 2000070242 A | 3/2000 |
| JP | 2000504854 A | 4/2000 |
| JP | 2001224853 A | 8/2001 |
| JP | 2001231904 A | 8/2001 |
| JP | 2001299975 A | 10/2001 |
| JP | 2002112984 A | 4/2002 |
| JP | 2002253718 A | 9/2002 |
| JP | 2002291952 A | 10/2002 |
| JP | 2003290406 A | 10/2003 |
| JP | 2004089727 A | 3/2004 |
| JP | 3656853 B2 | 6/2005 |
| JP | 2005198818 A | 7/2005 |
| JP | 2006167313 A | 6/2006 |
| JP | 2006263002 A | 10/2006 |
| JP | 2006320424 A | 11/2006 |
| JP | 2007144107 A | 6/2007 |
| JP | 2008295746 A | 12/2008 |
| JP | 2009048757 A | 3/2009 |
| JP | 2009050699 A | 3/2009 |
| JP | 2009172315 A | 8/2009 |
| JP | 2009201672 A | 9/2009 |
| JP | 2009213656 A | 9/2009 |
| JP | 2009213782 A | 9/2009 |
| JP | 2009219828 A | 10/2009 |
| JP | 2010502368 A | 1/2010 |
| JP | 2010246636 A | 11/2010 |
| KR | 20030041034 A | 5/2003 |
| KR | 20090084035 A | 8/2009 |
| WO | 9729814 | 8/1997 |
| WO | 2004073494 | 9/2004 |
| WO | 2009043024 A1 | 4/2009 |

(56) References Cited

FOREIGN PATENT DOCUMENTS

| WO | 2009/073607 A2 | 6/2009 |
| WO | 2010/121166 A1 | 10/2010 |
| WO | 2012/071548 A1 | 5/2012 |
| WO | 2012/071551 A1 | 5/2012 |
| WO | 2012061804 A1 | 5/2012 |

OTHER PUBLICATIONS

United States Patent and Trademark Office, "Final Office Action," issued in connection with U.S. Appl. No. 13/304,056, mailed Jan. 28, 2014, 13 pages.

May 31, 2013 (WO)—International Search Report and Written Opinion—App. No. PCT/US2012/066070.

Feb. 23, 2012 W(O)—International Search Report and Written Opinion—App. No. PCT/US2011/062117.

Feb. 20, 2014 (WO)—International Search Report and Written Opinion—App. No. PCT/US2013/067512.

Sep. 12, 2013(WO)—ISR and WO—App. No. PCT/US2013/044109.

Zhao, et al., Design and Practice for Individual Specialized PC Expert System for College Student, Journal of Xi An Institute of Physical Education, vol. 22, No. 2 (Mar. 2005) pp. 118-121.

United States Patent and Trademark Office, "Non-Final Office Action," issued in connection with U.S. Appl. No. 13/894,088, mailed Aug. 6, 2013, 5 pages.

International Bureau, "International Preliminary Report on Patentability," issued in connection with international application serial No. PCT/US2011/064711, mailed Jun. 27, 2013, 6 pages.

International Searching Authority, "International Search Report and Written Opinion," issued in connection with international application serial No. PCT/US2012/066065, mailed May 29, 2013, 10 pages.

International Bureau, "International Preliminary Report on Patentability," issued in connection with international application serial No. PCT/US2011/062114, mailed Jun. 6, 2013, 5 pages.

International Bureau, "International Preliminary Report on Patentability," issued in connection with international application serial No. PCT/US2011/062117, mailed Jun. 6, 2013, 6 pages.

International Bureau, "International Preliminary Report on Patentability," issued in connection with international application serial No. PCT/US2011/059559, mailed May 16, 2013, 6 pages.

United States Patent and Trademark Office, "Non-Final Office Action," issued in connection with U.S. Appl. No. 13/290,359, mailed Jun. 20, 2013, 11 pages.

United States Patent and Trademark Office, "Non-Final Office Action," issued in connection with U.S. Appl. No. 13/290,478, mailed Jun. 20, 2013, 8 pages.

United States Patent and Trademark Office, "Non-Final Office Action," issued in connection with U.S. Appl. No. 13/304,064, mailed Jun. 20, 2013, 10 pages.

International Searching Authority, "International Search Report and Written Opinion," issued in connection with international application serial No. PCT/US2011/059559, mailed Feb. 23, 2012, 13 pages.

International Searching Authority, "International Search Report and Written Opinion," issued in connection with international application serial No. PCT/US2011/064711, mailed Apr. 3, 2012, 9 pages.

\* cited by examiner

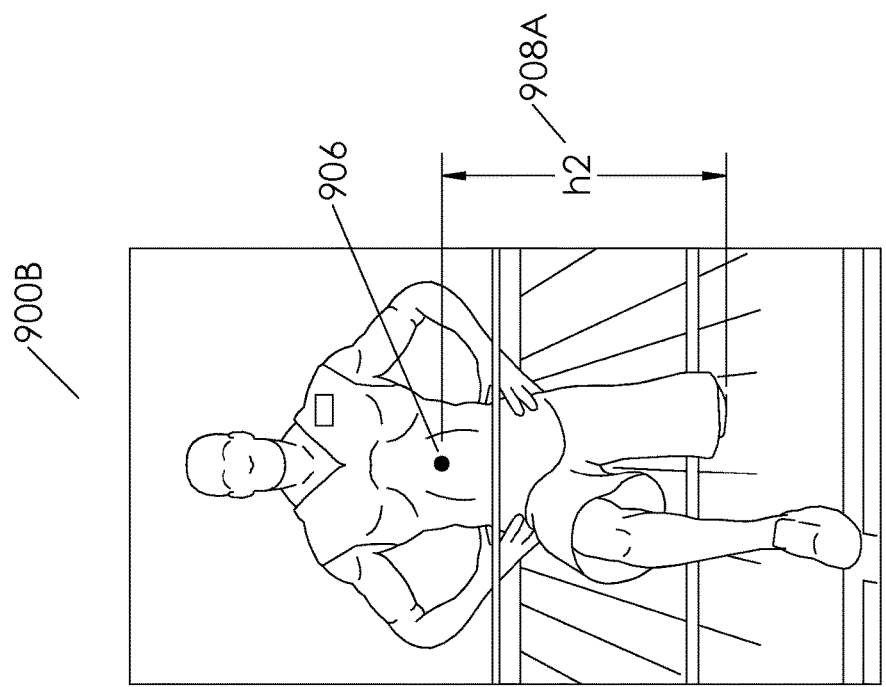
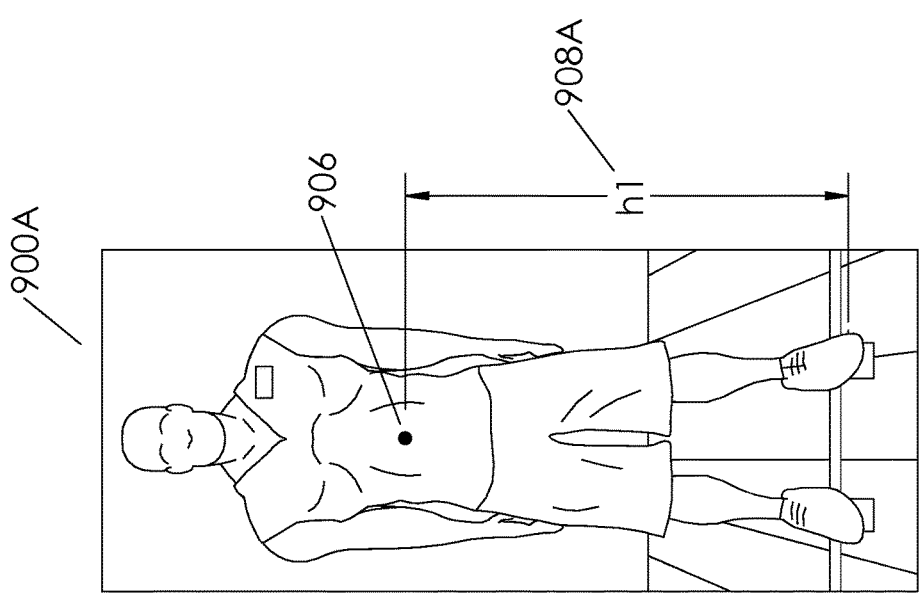
FIG. 10B
FIG. 10A

PROCESSING DATA OF A USER PERFORMING AN ATHLETIC ACTIVITY TO ESTIMATE ENERGY EXPENDITURE

CROSS REFERENCE TO RELATED APPLICATIONS

This application is a continuation-in-part of U.S. patent application Ser. No. 13/290,359 filed Nov. 7, 2011 titled "Method and System for Automated Personal Training," of U.S. patent application Ser. No. 13/304,064 filed Nov. 23, 2011 titled "Method and System for Automated Personal Training That Includes Training Programs," and of U.S. patent application Ser. No. 13/304,056 filed Nov. 23, 2011 titled "Fatigue Indices and Uses Thereof." This application claims the benefit of, and priority to, U.S. Provisional Patent 61/422,511 filed Dec. 13, 2010, 61/432,472 filed Jan. 13, 2011, and 61/433,792 filed Jan. 18, 2011, each of which is entitled "Method and System for Automated Personal Training" The contents of each of the above-identified applications are expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to processing of data taken while a user performs an athletic activity to determine an estimate of energy expenditure such as, for example, an amount of calories burned.

Example embodiments may relate to a system, method, apparatus, and computer readable media configured for prompting a user to perform an exercise, monitoring form of the user while performing the exercise, and calculating an energy expenditure estimate for the user performing the exercise based on a type of the exercise and on the form of the user. In other embodiments, expenditure estimate may be, or comprise, for example, an estimate of calories burned by the user. In certain embodiments, energy expenditure calculations comprise determinations relating to: effort, oxygen consumed, and/or oxygen kinetics of the user.

In various aspects, a system, method, apparatus, and/or computer readable media may be configured for processing data captured of a user performing an athletic activity over a time interval, and determining a location of a center of mass of a body part, body region, or entire body of the user at a first time instant and at a second time instant within the time interval. In further aspects, a system, method, apparatus, and/or computer readable media may be configured for identifying a change in the location of the center of mass from the first time instant to the second time instant, and calculating an energy expenditure estimate for the user due to the change.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments.

FIGS. 9, 10A-B, and 11 illustrate example locations of centers of mass for a virtual avatar of user, in accordance with example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
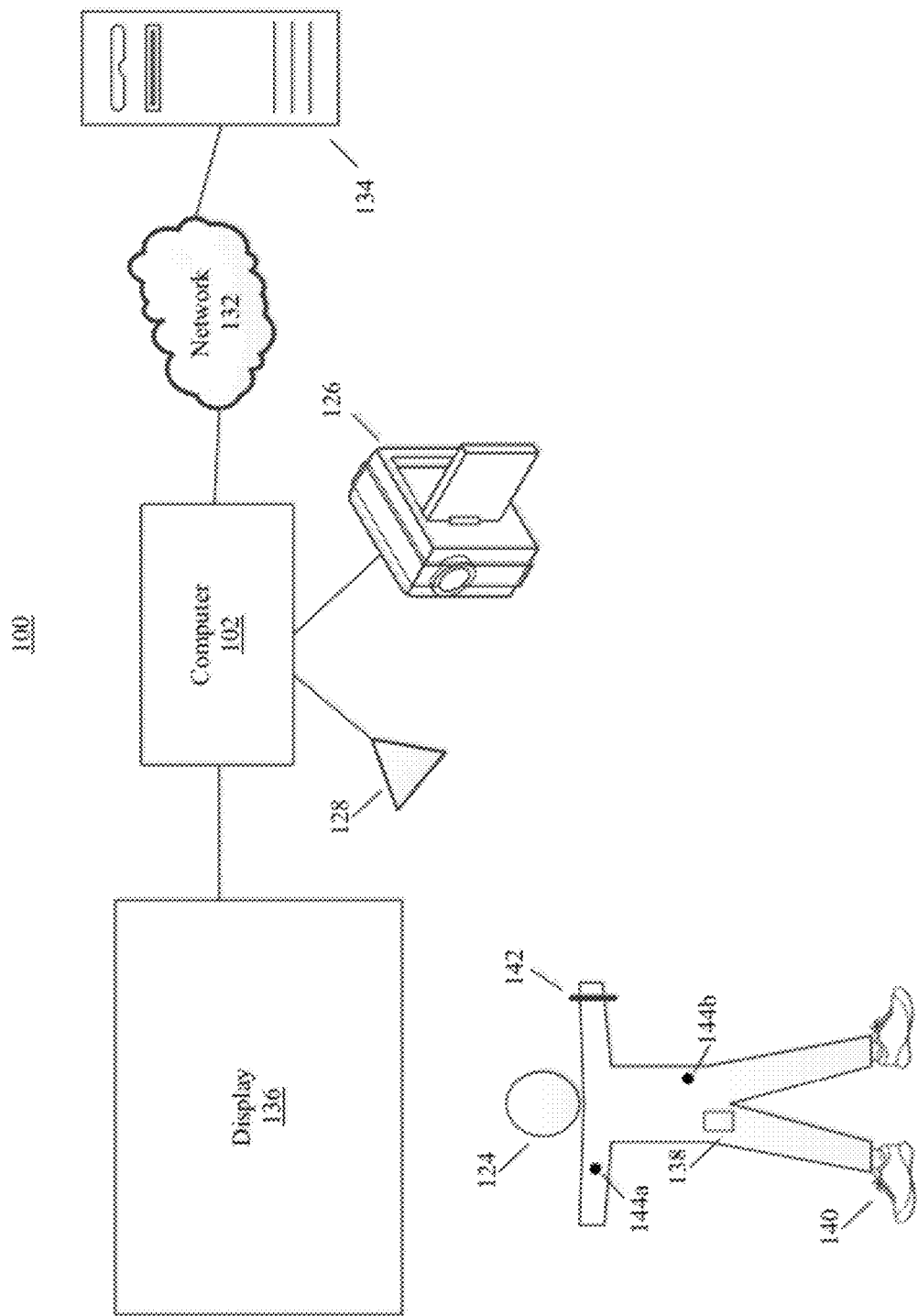

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
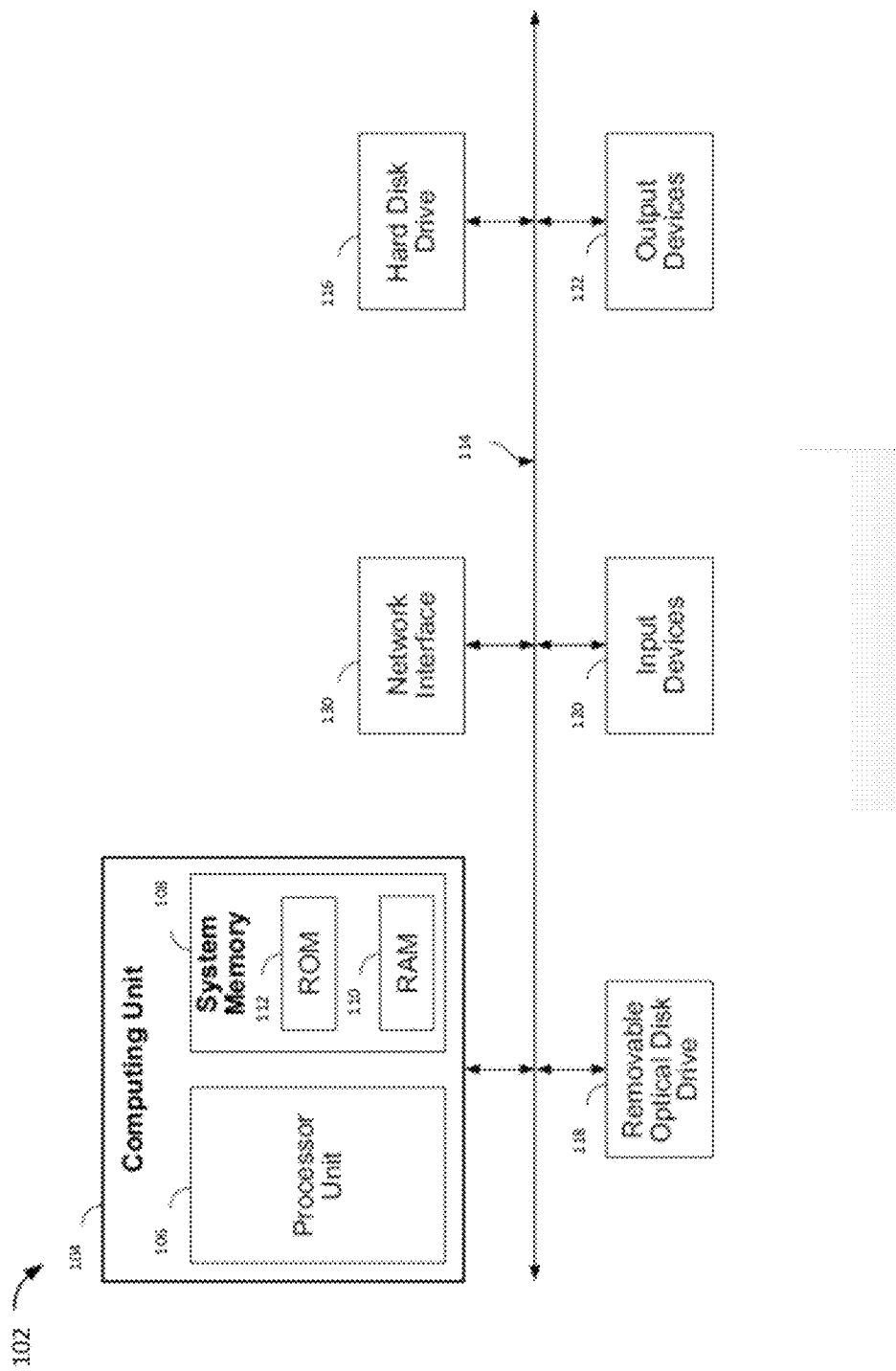

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. For example, and with reference to FIG. 4, image data from image-capturing device 126 may detect that the distance between sensor locations 402g and 402i has decreased and therefore, image-capturing device 126 alone may be configured to detect that user's 124 right arm has moved. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C., entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Still further, computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may communicate through computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

ii. Wrist-Worn Device

Figure 2B:
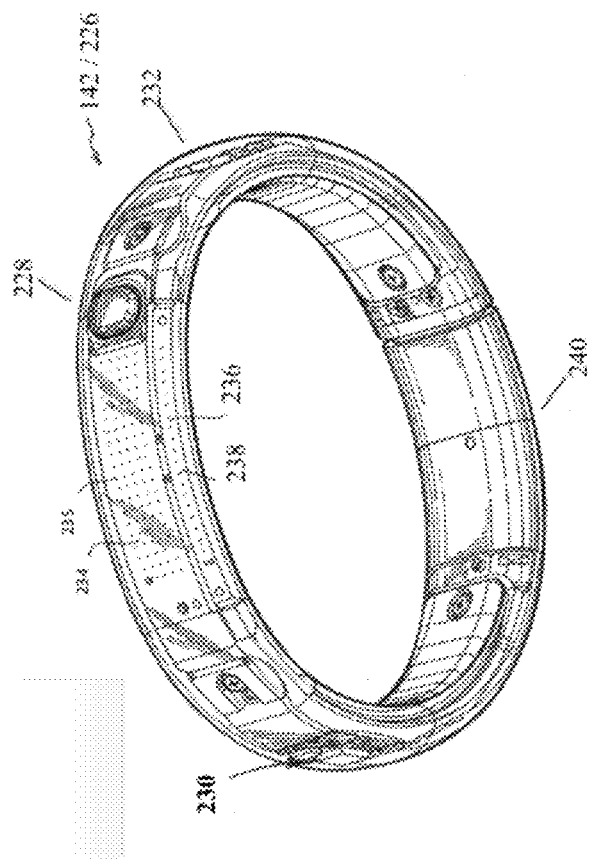
FIGS. 2A-B illustrate example sensor assemblies that may be worn by a user in accordance with example embodiments.
Figure 2A:
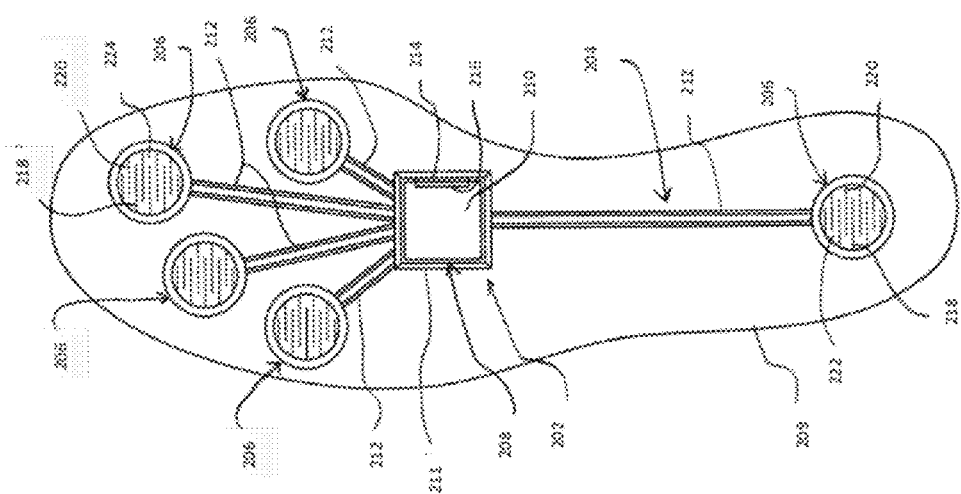

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and energy expenditure such as calories, heart rate, sweat detection, effort, oxygen consumed, and/or oxygen kinetics. Such parameters may also be expressed in terms of activity points or currency earned by the user based on the activity of the user.

I. Illustrative Athletic Monitoring Methods

System 100 may prompt a user to perform one or more exercises, monitor user movement while performing the exercises, and provide the user with an energy expenditure estimate based on their movement. System 100 may analyze a user's form to determine if the user is making an exercise more or less difficult, and adjust the energy expenditure estimate accordingly. Energy expenditure estimates may be, or comprise, an estimate of calories burned by the user. In certain embodiments, energy expenditure determinations may be based on, and/or conveyed as a point system. In one embodiment, calories may be converted to a point system, yet in other embodiments, measurements may be directly obtained in one or more point systems. In one implementation, activity points may be based upon: form, body movements, and/or completion of certain activities. In further embodiments, energy expenditure calculations may comprise determinations relating to: effort, oxygen consumed, and/or oxygen kinetics of the user. In one embodiment, computer 102, camera 126, sensor 128, and display 136 may be implemented within the confines of a user's residence, although other locations, including gyms and/or businesses are contemplated. Further, as discussed above, computer 102 may be a portable device, such as a cellular telephone, therefore, one or more aspects discussed herein may be conducted in almost any location. In this regard, the example embodiments of this disclosure are discussed in the context of being implemented with one or more of the example components of system 100. Those skilled in the art will appreciate that reference(s) to a particular component, such as computer 102, is not meant to be limiting, but rather to provide an illustrative example of one of many possible implementations. Thus, although certain components may be referenced, it is to be assumed that other components of system 100 may be utilized unless expressly disclaimed or physically impossible. Further, aspects disclosed herein are not limited to example system 100.

A. Monitoring User Movements

Figure 3:
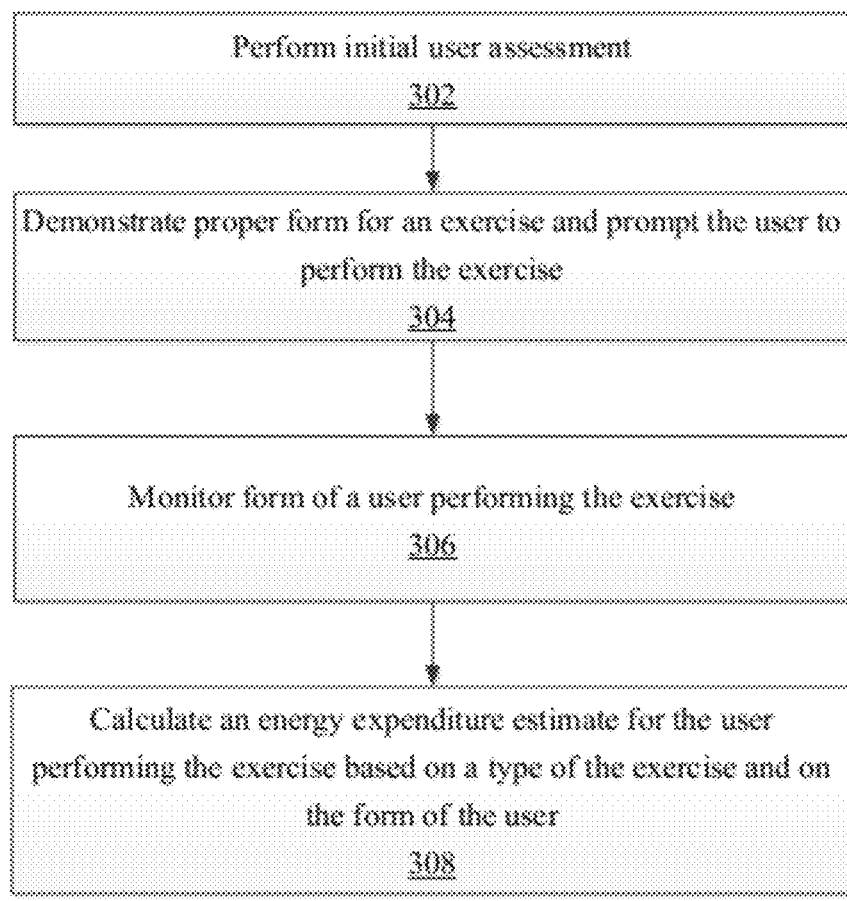
FIG. 3 illustrates an example flow diagram of a method for calculating an energy expenditure estimate for a user that accounts for a user's form while exercising as part of the estimate, in accordance with example embodiments.

While exercising, the system 100 may use one or more techniques to monitor user movement. FIG. 3 illustrates an example flow diagram of a method for calculating an energy expenditure estimate for a user that accounts for a user's form while exercising as part of the estimate, in accordance with example embodiments. The method may be implemented by a computer, such as, for example, computer 102, device 138, 140 and/or 142, as well as or other apparatuses. The blocks shown in FIG. 3 may be rearranged, some blocks may be removed, additional blocks may be added, each block may be repeated one or more times, and the flow diagram may be repeated one or more times. The flow diagram may begin at block 302.

1. Perform User Assessment

In block 302, the method may include performing an initial assessment of the user. A user, such as user 124, may be positioned in range of a sensor, such as in front of the image capturing device 126 and/or sensor 128, which may comprise an infrared transceiver. Display 136 may present a representation of user 124 that may be a "mirror-image" or depict a virtual avatar, such as a user avatar, that moves to correspond with user movement. Computer 102 may prompt the user to move into a certain region relative to the image capturing device 126 and/or relative to the infrared transceiver 128 so that the user is within frame and/or range. When properly positioned, system 100 may process movement of the user. Although the term "initial" has been utilized, this assessment may occur each time the user initiates system 100, performs certain movements, upon passage of time, or for any other reason. Thus, references to assessments herein are not limited to a single assessment.

a. Identify Sensory Locations

Figure 4:
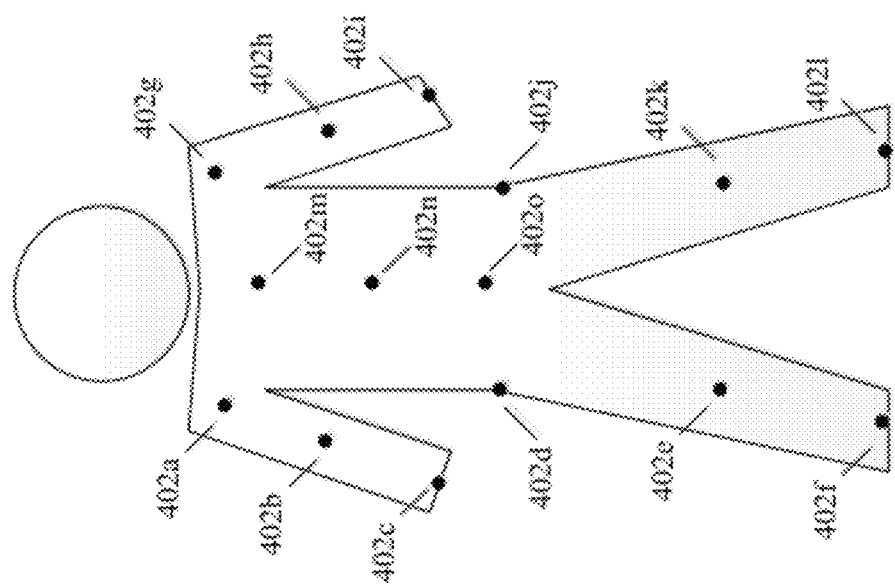
FIG. 4 illustrates example points on a user's body for monitoring during exercising in accordance with example embodiments.

System 100 may process sensory data to identify user movement data. In one embodiment, sensory locations on a user's body may be identified. With reference to FIG. 4, sensory locations 402a-402o may correspond to locations of interest on the user's 124 body (e.g., ankles, elbows, shoulders, etc.). For example, images of recorded video, such as from camera 126, may be utilized in an identification of the sensory locations 402a-402o. For example, the user may stand a certain distance, which may or may not be predefined, from the camera 126, and system 100 may process the images to identify the user 124 within the video, for example, using disparity mapping techniques. In an example, image capturing device 126 may be a stereo camera having two or more lenses that are spatially offset from one another and that simultaneously capture two or more images of the user. System 100 may process the two or more images taken at a same time instant to generate a disparity map for determining a location of certain parts of the user's body in each image (or at least some of the images) in the video using a coordinate system (e.g., Cartesian coordinates). The disparity map may indicate a difference between an image taken by each of the offset lenses.

In a second example, one or more sensors may be located on or proximate to the user's 124 body at the sensory locations 402a-402o or the user 124 may wear a suit having sensors situated at various locations. Yet, in other embodiments, sensor locations may be determined from other sensory devices, such as devices 138, 140 and/or 142. In this regard, sensors may be physical sensors located on a user's clothing, yet in other embodiments, sensor locations 402a-402o may be based upon identification of relationships between two moving body parts. For example, sensor location 402a may be determined by identifying motions of user 124. In this regard, the overall shape or portion of a user's body may permit identification of certain body parts. Regardless of whether a camera, such as camera 126, is utilized and/or a physical sensor located on the user 124, such as sensors within device(s) 138, 140, 142 are utilized, the sensors may sense a current location of a body part and/or track movement of the body part.

In certain embodiments, a time stamp may be added to the data collected (such as collected part of block 302 in FIG. 3) indicating a specific time when a body part was at a certain location. Sensor data may be received at computer 102 (or other device) via wireless or wired transmission. A computer, such as computer 102 and/or devices 138, 140, 142, may process the time stamps to determine the locations of the body parts using a coordinate system (e.g., Cartesian coordinates) within each (or at least some) of the images in the video. Data received from camera 126 may be corrected, modified, and/or combined with data received from one or more other devices 138, 140, and 142.

In a third example, system 100 may use infrared pattern recognition to detect user movement and locations of body parts of the user 124. For example, sensor 128 may include an infrared transceiver, which may be part of camera 126, or another device, that may emit an infrared signal to illuminate the user's 124 body using infrared signals. The infrared transceiver 128 may capture a reflection of the infrared signal from the body of user 124. Based on the reflection, the system 100 may identify a location of certain parts of the user's body using a coordinate system (e.g., Cartesian coordinates) at particular instances in time. Which and how body parts are identified may be predetermined based on a type or types of exercise a user is requested to perform.

Figure 5:
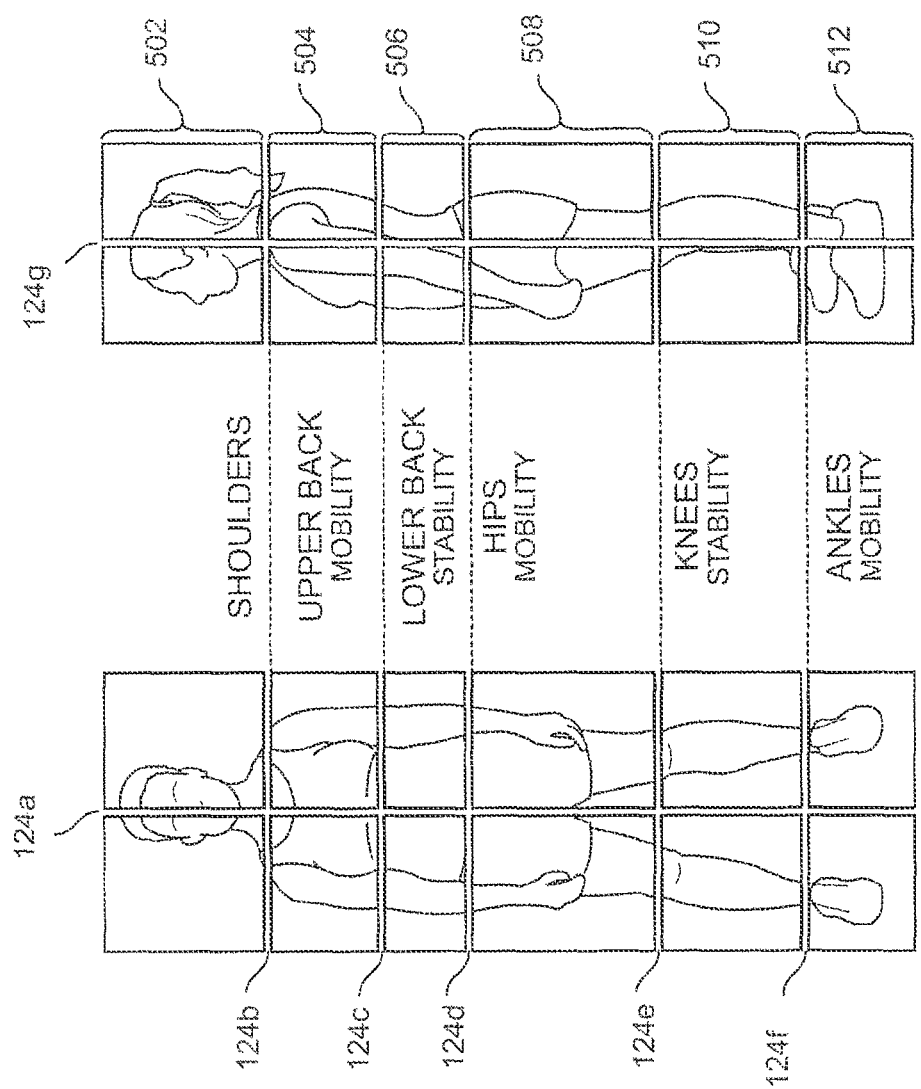
FIG. 5 illustrates an example posture assessment in accordance with example embodiments.

As part of a workout routine, system 100 may make an initial postural assessment of the user 124 as part of the initial user assessment in block 302 of FIG. 3. With reference to FIG. 5, system 100 may analyze front and side images of a user 124 to determine a location of one or more of a user's shoulders, upper back, lower back, hips, knees, and ankles. On-body sensors and/or infrared techniques may also be used, either alone or in conjunction with camera 126, to determine the locations of various body parts for the postural assessment. For example, system 100 may determine assessment lines 124*a*-*g* and/or regions 502-512 to determine the locations of a various points on a user's body, such as, for example, ankles, knees, hips, upper back, lower back, and shoulders.

b. Identify Sensory Regions

In further embodiments, system 100 may identify sensory regions (see, e.g., block 302). In one embodiment, assessments lines 124*a*-*g* may be utilized to divide the user's body into regions. For example, lines 124*b*-*f* may be horizontal axes. For example, a "shoulders" region 502 may correlate to a body portion having a lower boundary around the user's shoulders (see line 124*b*), region 504 may correlate to the body portion between the shoulders (line 124*b*) and about half the distance to the hips (see line 124*c*) and thus be an "upper back" region, and region 506 may span the area between line 124*c* to the hips (see line 124*d*) to comprise a "lower back region." Similarly, region 508 may span the area between the "hips" (line 124*d*) and the "knees" (see line 124*e*), region 510 may span between lines 124*e* and 124*f* and region 512 (see "ankles") may have an upper boundary around line 124*f*. Regions 502-512 may be further divided, such as into quadrants, such as by using axes 124*a* and 124*g*. To aid in the identification of one or more sensory regions, system 100 may prompt the user to make one or more specific movements. For example, system 100 may prompt a user to move a specific body part or region (e.g., wave their right arm, or wave the left arm in a specific pattern) to aid the system 100 (e.g., computer algorithm processing information received from the infrared transceiver 128) in determining which body part or region is in a specific location within a coordinate system.

c. Categorize Locations or Regions

In certain embodiments, body parts or regions that are not proximate to each other may nonetheless be categorized into the same movement category (see, e.g., block 302). For example, as shown in FIG. 5, the "upper back", "hips", and "ankles" regions 504, 508, 512 may be categorized as belonging to a "mobility" category. In another embodiment, the "lower back" and "knees" regions 506, 510 may be categorized as belonging to a "stability" category. The categorizations are merely examples, and in other embodiments, a location or region may belong to multiple categories. For example, a "center of gravity" region may be formed from regions 504 and 506. In one embodiment, a "center of gravity" may comprise portions of regions 504 and 506. In another embodiment, a "center of moment" category may be provided, either independently, or alternatively, as comprising a portion of at least another category. In one embodiment, a single location may be weighted in two or more categories, such as being 10% weighted in a "stability" category and 90% weighted in a "mobility" category.

System 100 may also process the image to determine a color of clothing of the user or other distinguishing features to differentiate the user from their surroundings. After processing, system 100 may identify a location of multiple points on the user's body and track locations of those points, such as locations 402 in FIG. 4. System 100 may also prompt the user to answer questions to supplement the postural assessment, such as, for example, age, weight, etc. Again, block 302 is optional and is not required in accordance with various embodiments.

2. Providing Form

With reference again to FIG. 3, in block 304, various embodiments may include demonstrating proper form for an exercise and prompting the user to perform the exercise. For example, after or in addition to the initial postural assessment, the system 100 (such as with computer 102) may cause the display 136 to present a virtual trainer demonstrating an exercise to instruct the user on proper form and/or may present a depiction and/or an actual video of a real person demonstrating proper form for an exercise. System 100 may then prompt the user to begin performing the exercise.

Figure 6:
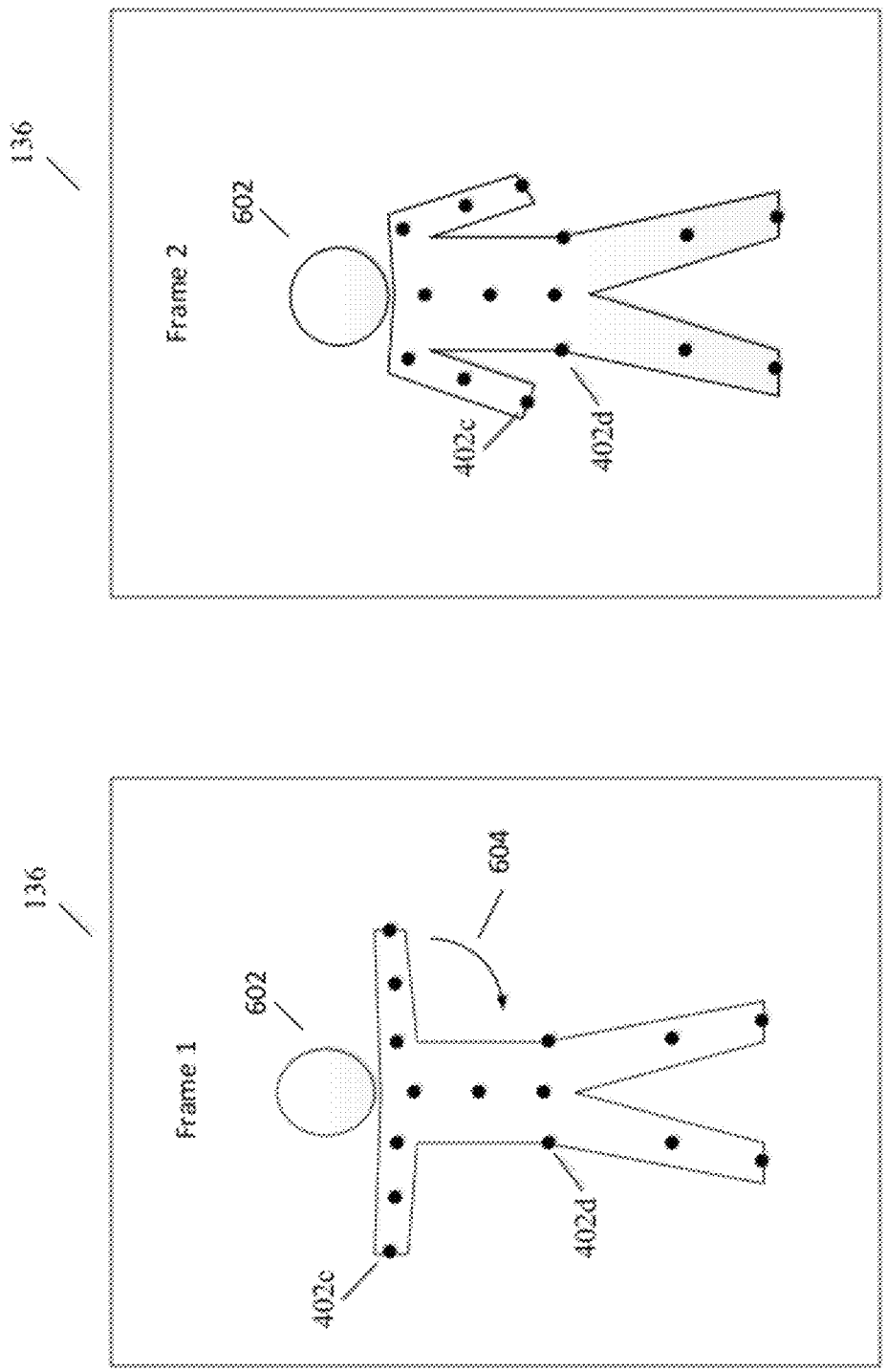
FIG. 6 illustrates example displays of a virtual avatar of a user performing an exercise in accordance with example embodiments.

With reference to FIG. 3, in block 306, various embodiments may include monitoring form of a user performing the exercise. As seen in FIG. 6, system 100, such as through computer 102, may cause the display 136 to present a virtual avatar 602 of the user. The virtual avatar 602 may move in synchronism with the user 124. Also, the display 136 may present video of the actual user, rather than avatar 602. System 100 may process one or more frames in the video to determine at least some of the sensory locations 402, or may receive data from sensors worn on-body by the user. As shown in FIG. 6, sensory locations 402 may be displayed on the virtual avatar.

For proper form during many exercise routines, a user may proceed through multiple positions during a repetition of an exercise. Certain aspects disclosed herein relate to defining one or more measurement positions and/or desired locations for one or more sensory locations 402. For example, a measurement position may refer to a particular relationship between various body parts during a repetition. For example, a measurement position may indicate a desired location for a user's body part (e.g., desired location of user's left elbow) and may indicate a desired relationship between multiple body parts (e.g., angle between a user's torso and thigh). For a movement or series of movements (such as an exercise routine), system 100 may define one or more measurement positions and/or desired locations for one or more of the sensory locations 402 for a measurement position. In various implementations, each repetition of an exercise can be broken down into one or more measurement positions.

System 100, such as through computer 102, may process video or sensor data of a user performing an exercise to determine when a user's body has reached a measurement position. For each measurement position, system 100 may compare the measured sensory locations to desired sensory locations to monitor the user's form while performing the exercise. For example, frame 1 of FIG. 6 may correspond to a first measurement position and frame 2 may correspond to a second measurement position. System 100 may determine a distance between sensory locations 402c and 402d at each measurement position. Other relationships between sensory locations may be specified (e.g., certain angle, certain position, etc.)

With reference again to FIG. 3, in block 308, various embodiments may include calculating an energy expenditure estimate for the user. Calculations may be based on a type of the exercise and/or on the form of the user. The energy expenditure estimate may be, or comprise, for example, an estimate of calories burned by the user. In certain embodiments, energy expenditure calculations comprise determinations relating to: effort, oxygen consumed, and/or oxygen kinetics of the user. During a workout session or upon its completion, the system 100 may inform the user of energy expended. In one embodiment, system 100 may provide an indication of a quantity of calories they have burned. To provide a more accurate calories burned estimate, system 100 may account for a user's form while performing an exercise as well as the type of exercise that was performed. Further embodiments may utilize user attributes to more accurately identify a number of calories burned by a user. Example user attributes may be height, weight, age, etc. One or more sensors may determine the user attributes, or the user may input the user attributes via an interface to a computer, such as computer 102.

System 100 may use information from sensory locations 402 detected at measurement positions of an exercise in combination with one or more known values to obtain a more accurate determination of calories burned. In one embodiment, a known value may comprise or be part of a Metabolic Equivalent of Task (MET) table. A MET table, for example, may be defined for a particular exercise (e.g., squat, lunge, etc.) and used to determine how many calories a user burned during a workout. System 100 may store or have access to multiple MET tables corresponding to different exercises (e.g., squat, lunge, jumping rope, push up, running, etc.). System 100 may process data from the video and/or sensors to determine a number of repetitions of an exercise that a user has performed or duration of an exercise, and may estimate a number of calories burned by the user based on the repetitions and/or duration information and the one or more known values, such as may be obtained from MET tables.

MET tables, however, are statistical averages and are not as accurate as they could be. Thus, conventional calorie measurement systems that rely on MET tables merely provide a user with a rough estimate of how many calories they burned during a workout. Although embodiments of this disclosure may utilize one or more values from a MET table, aspects of this disclosure are not limited by the deficiencies of prior measurements systems. For example, in one embodiment the user's form may be accounted for. System 100 may apply a scaling factor to a calories burned estimate based on detected sensory location information. The scaling factor may reflect how well a user has performed an exercise and in certain embodiments may consider attributes of the user. For example, the scaling factor may be a function of one or more of the sensory location information, a duration during which the user performed an exercise, information reported by the user (e.g., age, weight), a user's heart rate taken by a heart rate monitor, a pressure measurement, and/or other data. A pressure measurement may be obtained from pressure sensor 140 located in a shoe, for example, to determine how much force a user exerts during movement. For example, a user may be holding a weight in each hand and the pressure sensor 140 may monitor pressure at the shoe. The pressure sensor 140 may also indicate how quickly a user changes direction (e.g., how hard a user made a cut) or how much power was exerted when jumping.

To determine the scaling factor, system 100 may monitor for relationships between one or more body parts at one or more measurement positions during a repetition of an exercise. Modifications to these relationships may make an exercise easier or harder to perform. The scaling factor may consider factors indicative of whether a user is making the exercise more or less difficult to complete, and may adjust a calories burned estimate accordingly. In a squat, for example, relationships may be defined for a first angle between a user's torso and thighs, and a second angle between a user's thighs and shin while performing the squat. System 100 may process sensory location information to measure the first and second angle of the user over time for comparison with the desired first and second angle.

Figure 7B:
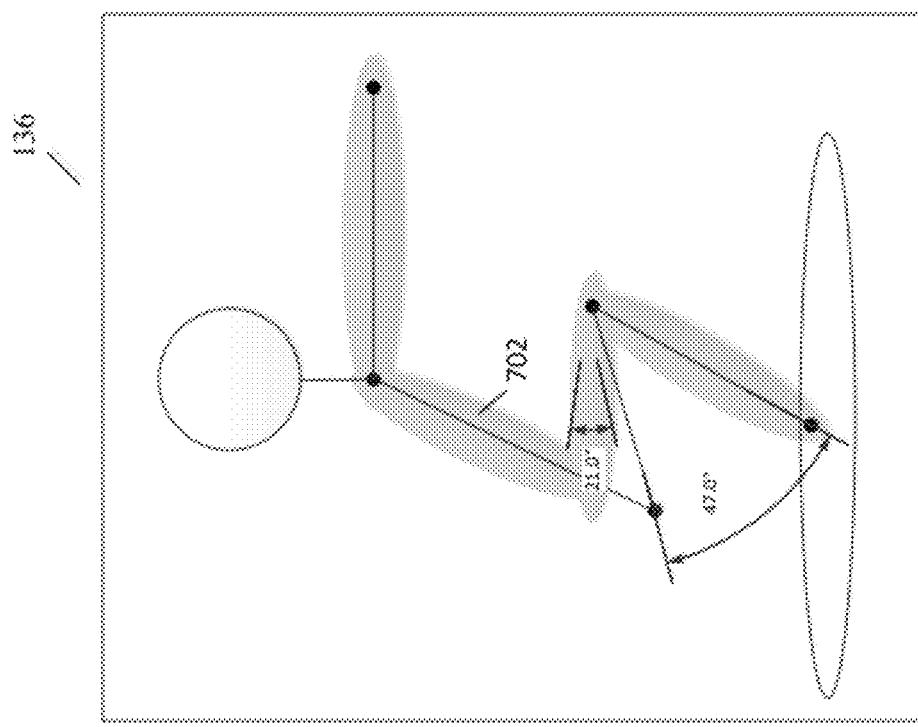
FIGS. 7A-B illustrate example displays of a virtual avatar of a user performing a squat in accordance with example embodiments.
Figure 7A:
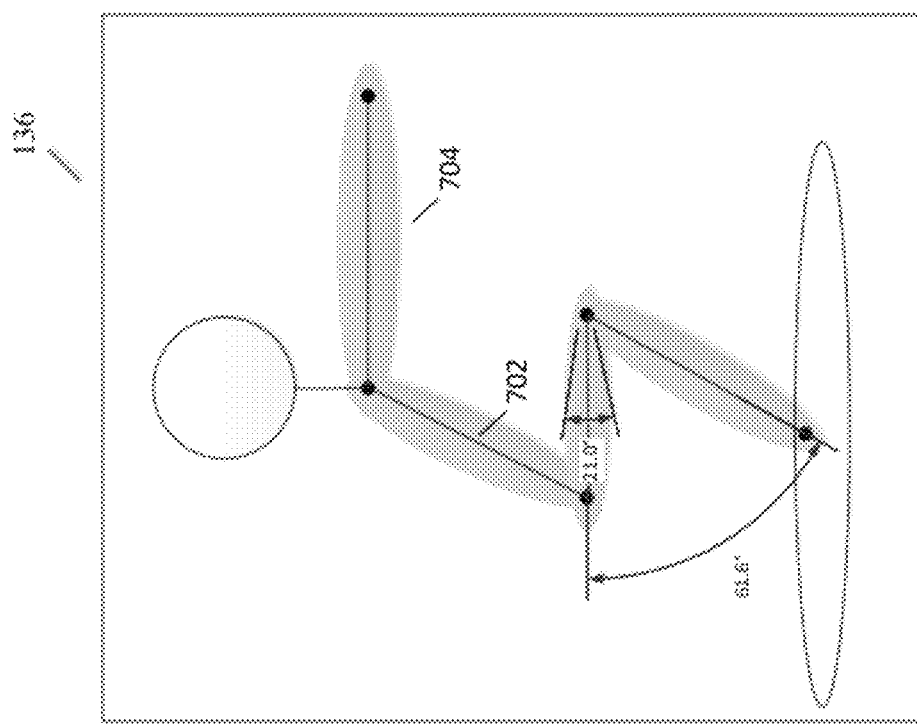

In an example, with reference to FIGS. 7A-B, a virtual avatar 702 of a user is displayed performing a squat. Virtual avatar 702 is depicted as a stick figure, and proper technique for an exercise is shown as a shaded region 704. At the lowest part of the squat (for example, as shown in FIG. 7A), the desired form may specify a relationship between a user's thigh and shin, between a user's back and arms, and/or any other two parts or locations the user. In one embodiment, the desired form may specify a first predetermined angle between a location or part. For example, a user's upper leg and lower leg, and/or a second predetermined angle between a user's back and arms. System 100 may process the sensory location information to compare the user's form to the desired form. For example, system 100 may process the sensory location information to determine an angle between the user's thigh and shin, and an angle between the user's back and arms when performing a squat.

System 100 may define thresholds for the relationships between various body parts for adjusting the scaling factor. The thresholds may permit the user's form to differ by a certain amount from the desired form. For a preferred threshold, system 100 may determine that the user has good form that does not require any adjustment of the scaling factor (e.g., less than a 5% difference between angle between the user's upper leg and lower leg and desired angle). For an acceptable threshold, the system 100 may nominally adjust the scaling factor upward or downward to reflect increased or reduced effort by the user (e.g., 5-15% difference between angle between the user's upper leg and lower leg and desired angle). For an unacceptable threshold, the system 100 may determine that the user's form has reduced the amount of effort to perform the exercise and may downwardly adjust the scaling factor (e.g., greater than a 15% difference between angle between the user's upper leg and lower leg and desired angle).

System 100 may also adjust the scaling factor based on omissions or additions a user makes when performing an exercise. For example, a user may not be doing an arm movement in an exercise that requires movement of both arms and legs. Also, if the user is performing an additional movement beyond what is specified for an exercise, the system 100 may adjust the scaling factor to increase the calorie estimate.

Upon determining the scaling factor, the system 100 may determine an amount of calories burned as a function of the scaling factor(s) and the calorie estimate. The function may be a multiplication of the calorie estimate by the scaling factor, or via other relationships. For example, the scaling factor may be adjustments to a number of variables in a mathematical equation for adjusting calories burned by one or more of multiplication, addition, and subtraction. In further embodiments, system 100 may cease determinations relating to caloric expenditure if the user deviates from a threshold. For example, a user may be interrupted during a workout routine and either forget or be too distracted to "pause" the determination, thus, certain embodiments may cease determining caloric expenditure upon detecting that a user is not performing an exercise. Further embodiments may cease or otherwise alter determinations of caloric expenditure if one or more variation thresholds are exceeded, such as for example, if a user is over-extending or under-extending a body region or part. In certain embodiments, if a user's movements are prone to cause injury, measurements and/or determinations relating to caloric expenditure may be stopped. In one implementation, system 100 may provide cues and/or instructions to correct the user's deficiencies or incorrect movements.

The following provides an example equation for calculating an amount of calories burned by a user during a workout.

$$\text{Calories burned} = \text{BMR} * (\text{Activity modifier}) * (\text{Completeness modifier}). \quad \text{Equation (1):}$$

In equation (1), BMR is an acronym for Basal Metabolic Rate. The system 100 may calculate the BMR using the Mifflin-St. Jeor Equation, BMR=(10*w)+(6.25*h)−(5.0*a)+(5 for men, −161 for women), where "*" is the multiplication symbol, "w"=weight in kilograms, "h"=height in centimeters, "a"=age in years. The system 100 may also use the Harris-Benedict equation instead of or, in addition to, the Mifflin-St. Jeor Equation.

The activity modifier may be an adjustment corresponding to a type of exercise being performed by a user. The activity modifier may be larger for more strenuous exercises, and smaller for less strenuous. System 100 may store a file containing activity modifiers, where each activity modifier may have a value for a particular exercise type. Two or more exercises may have activity modifiers with a same value, or certain exercise may have a unique value for the activity modifier. The activity modifier may have a default value. In one example embodiment, the default value may be 0.1. In a second embodiment, the default value may be 1.0. The default value may be any value, including 0.0. System 100 may update the default value to correspond to the activity modifier for an exercise currently being performed by the user. Over a duration of the workout, system 100 may use different ones of the activity modifiers to calculate calories burned using equation (1) corresponding to different exercises the user is prompted to perform. One or more factors may contribute to the activity modifier and/or adjustment of the modifier. Examples include, but are not limited to: pace, type of exercise, duration, and combinations thereof. Further, activity modifiers and/or variation of activity modifiers may be determined from predetermined values (such as a value assigned to an exercise or movement that a user is prompted to perform), the user's performance, information from a MET table on a particular exercise, and combinations thereof The completeness modifier may be used for adjusting the BMR based on how well a user's form corresponds to a desired form when performing an exercise. In an example, the completeness modifier may indicate what percentage of full movement was achieved for each repetition when performing an exercise (e.g., determine a percentage of a measured angle between the user's torso and thighs for a particular repetition of an exercise relative to a desired angle), or may be an average of the percentage of full movement for a predetermined number of repetitions (e.g., last three exercises, last five exercises, all exercises, etc.). The completeness modifier may have a default value. In one example embodiment, the default value may be 0.1. In a second embodiment, the default value may be 1.0. The default value may be any value, including 0.0. System 100 may update the completeness modifier over time based on how well the user's form conforms to a desired form. One or more factors may contribute to the activity modifier and/or adjustment of the modifier. Examples include, but are not limited to: pace, type of exercise, duration, and combinations thereof. Further, activity modifiers and/or variation of activity modifiers may be determined from predetermined values (such as a value assigned to an exercise or movement that a user is prompted to perform), the user's performance, and combinations thereof Equation (2), provided below, may be utilized in further embodiments.

$$\text{Calories burned} = \text{BMR} * (\text{Activity modifier}) * (\text{Completeness modifier}) * (\text{Multiply Modifier}) + (\text{Addition Modifier}) \quad \text{Equation (2):}$$

Values for BMR, Activity Modifier, and/or Completeness Modifier of Equation (2) may be determined in accordance with one or more embodiments described above in reference to Equation (1). In one embodiment, the value of the Multiply Modifier may be defined for each type of exercise. In one example embodiment, the default value may be 0.1. In a second embodiment, the default value may be 1.0. The default value may be any value, including 0.0. System 100 may update the Multiply Modifier during a workout to correspond to a type of exercise the user is prompted to perform. In certain embodiments, the Activity Modifier may be obtained (either partially or entirely) from empirical data.

In certain embodiments, the value of the Addition Modifier may be defined for each type of exercise. In one example embodiment, the default value may be 0.1. In a second embodiment, the default value may be 1.0. The default value may be any value, including 0.0. System 100 may update the Addition Modifier during a workout to correspond to a type of exercise the user is prompted to perform. In certain embodiments, the Activity Modifier may be obtained (either partially or entirely) from empirical data.

System 100 may calculate the calories burned over a duration of a workout, which may incorporate the utilization of equations (1) or (2). System 100 may cause the display 136 to display a running total of calories burned. In certain embodiments, the total may be determined for one or more completed repetitions and one or more completed sets of each exercise. System 100 may also calculate and cause display of calories burned by type of exercise performed. Other information such as, for example, peak/minimum/average calorie burning rate by workout, by repetition, by set, or by exercise type may also be calculated and displayed. System 100 may periodically determine an amount of calories burned by the user while exercising using equation (1). System 100 may indicate a current amount of calories burned that is continually updated over a workout (e.g., a running total), or may update the calories burned amount at predetermined times (e.g., user completes a set of a first type of exercise and begins a set of second type of exercise, at the end of the workout session, etc.). System 100 may also inform the user how many calories were burned during each repetition as well as in each set of an exercise.

One or more of the inputs and/or variables used in the determination of caloric expenditure (such as with equation (1)) may remain the same regardless of the type of exercise being performed by the user, yet others may vary. For example, the BMR may be the same over the entire workout as a user's weight, height, and age do not change appreciably over the course of a workout. Further, one or more of the Activity modifier, Completeness modifier, Multiply Modifier, and Addition Modifier may vary over the workout. The values (and/or variation) of the values may depend on the type exercise currently being performed by the user.

The Completeness modifier may vary from repetition to repetition. As noted above, system 100 may generate the Completeness modifier based on monitoring a user's form while they perform an exercise. Generally, an exercise includes a sequence of motions to perform one repetition, and a user typically performs a set that includes two or more repetitions. A user's form may vary from repetition to repetition, and so may the Completeness modifier.

System 100 may determine calories burned using equation (1) based on a Completeness modifier that varies from repetition to repetition, or based on a filtered version of the Completeness modifier. To filter the Completeness modifier, the system 100 may, for example, determine a Completeness modifier for one or more repetitions, may average some or all of the Completeness modifiers, and may use the average in equation (1). Also, system 100 may generate the Completeness modifier as a weighted average, where Completeness modifiers of some repetitions may be given greater weight than others. For example, system 100 may apply a decaying function where more recent Completeness modifiers are weighted more heavily than less recent when generating an average.

System 100 may also allow a user to make desired movements, and calculate an amount of calories burned for such movement. In one embodiment, all detected movements may be utilized in calculations. Yet in other embodiments, only certain (e.g., system supported and/or those prompted to be performed) movements may be considered. System 100 may process data from image capturing device 126 and/or from various sensors to attempt to classify a user's movement. For example, system 100 may compare the user's movement to other known movements for which a MET table has been defined. If a user's movement corresponds to a known movement for which a MET table has been defined, then system 100 may use the identified MET table for calculating an amount of calories burned.

If the user's movement does not match an exercise defined by a MET table, the system 100 may identify one or more exercises that include movements similar to the movement being performed by the user. For example, system 100 may determine that the user's lower body moves similar to a squat and upper body moves similar to a pushup. System 100 may calculate the number of calories the user would burn using the identified MET tables as if the users were doing a squat, and as if they were doing a pushup, as approximations for the amount of calories burned by the user. In further embodiments, a new entry may be created. In this regard, certain embodiments may permit the entry and later identification of new movements and/or exercises. In certain embodiments, the user may provide inputs regarding an approximate caloric expenditure for an unidentified movement/exercise. Yet in other embodiments, system 100 may calculate caloric expenditure, such as from one or more sensors as discussed herein. In still yet further embodiments, system 100 may utilize one or more sensor readings as well as an input from a user (and/or third-party) in determining attributes, such as caloric expenditure, for previously unknown movements or exercises. Examples of estimating caloric expenditure without MET tables, may include but are not limited to, determining changes in potential energy. Examples of using changes in potential energy are provided in the next section.

System 100 may be configured to transmit calories burned estimates to a social networking website. The users may be ranked based on their total number of calories burned for a desired time interval (e.g., rank by day, week, month, year, etc.). With reference again to FIG. 3, the method may end or may return to any of the preceding blocks.

i. Energy Expenditure Estimate Based on Changes in Potential Energy

System 100 may also calculate an energy expenditure estimate of a user for physical activities not defined by a MET table. For example, system 100 may calculate an amount of calories burned by a user performing any desired combination of movements. During a workout, a user may be exposed to their own body weight and gravity. A location of a user's center of mass, or of a center of mass of a particular body part, may be utilized in estimating an amount of calories burned by the user performing an athletic activity.

Figure 8:
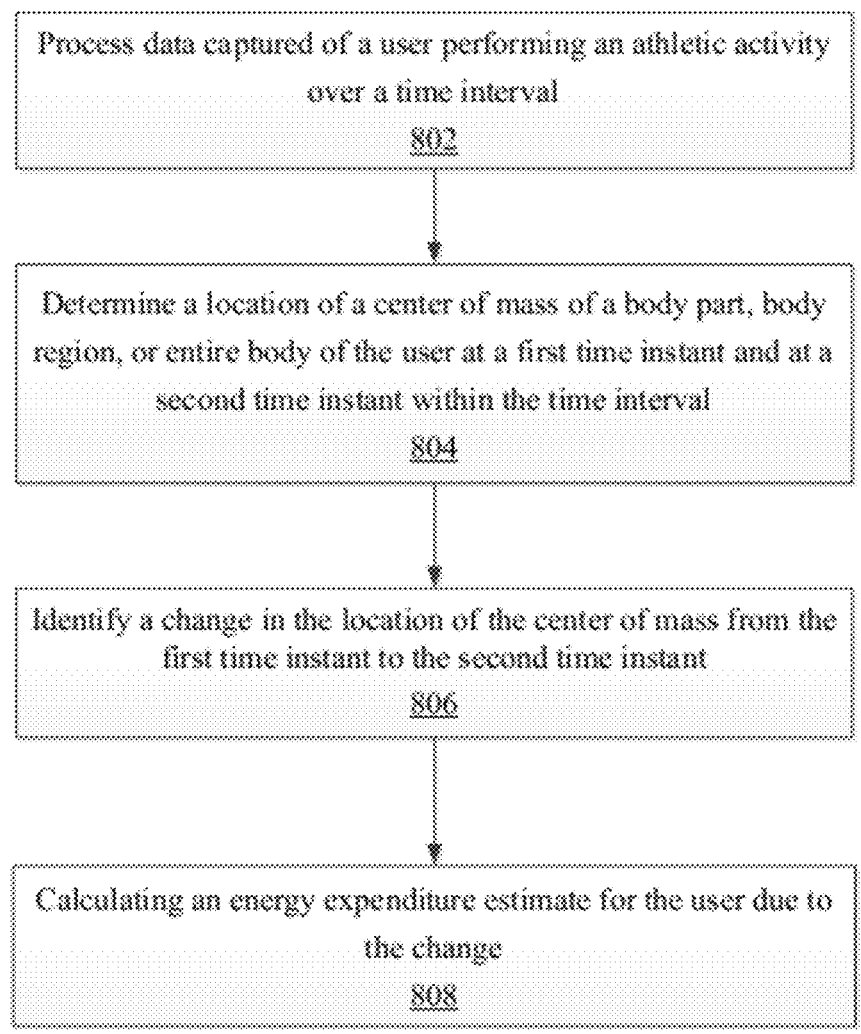
FIG. 8 illustrates an example flow diagram of a method for calculating an energy expenditure estimate for a user while performing an athletic activity based on monitoring changes in potential energy, in accordance with example embodiments.

FIG. 8 illustrates an example flow diagram of a method for calculating an energy expenditure estimate for a user while performing an athletic activity based on monitoring changes in potential energy, in accordance with example embodiments. The method may be implemented by a computer, such as, for example, computer 102, device 138, 140 and/or 142 as well as other apparatuses. The blocks shown in FIG. 8 may be rearranged, some blocks may be removed, additional blocks may be added, each block may be repeated one or more times, and the flow diagram may be repeated one or more times. The flow diagram may begin at block 802.

In block 802, various embodiments may involve processing data captured of a user performing an athletic activity over a time interval. In an example, system 100 may prompt a user to perform ten repetitions of a lunge and may process data captured of the user performing the lunge. The data may be video captured by the camera 126 or may be captured by the infrared transceiver 128, and/or by the other device sensors 138, 140, and 142.

Figure 9:
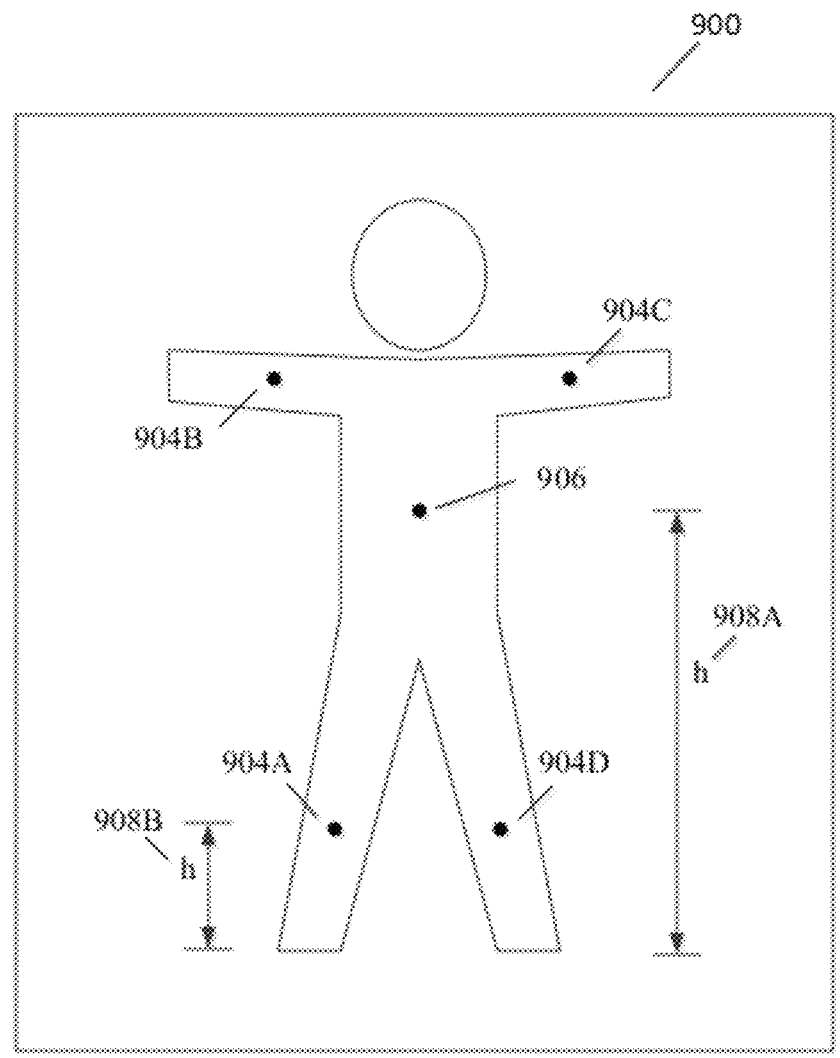

In block 804, various embodiments may involve determining a location of a center of mass of a body part, body region, or of an entire body of the user at a first time instant and at a second time instant within the time interval. Yet in other embodiments, a center of movement may be utilized. For simplicity purposes, however, a center of mass will be discussed. In an example, system 100 may instruct the user to place sensors at locations of corresponding to a center of mass for one or more body parts of the user. With reference to FIG. 9, one or more of center of mass locations may be at example locations 904A-D and 906, or at other locations on the user's body. Any number of locations may be monitored. At least one sensor may wirelessly transmit sensor data indicating a time and a location of the sensor (or location of a body part as detected by the sensor). A location may be coordinates in a coordinate system (e.g., Cartesian coordinate system) and may be associated with a time stamp indicating when the sensor was at a particular coordinate. In certain embodiments, system 100 may process the sensor data to periodically determine locations 904A-D and 906. For example, system 100 may receive sensor data, such as from device sensors 138, 140 and/or 142. Computer 102 (or another component of system 100) may process data as part of determining locations (such as locations 904A-D and 906). In one embodiment, data may be processed on a routine ongoing-basis, such as four times per second. In another example, computer 102 (or another component of system 100) may process data from image capturing device 126 to determine locations 904A-D and/or 906.

Figure 11:
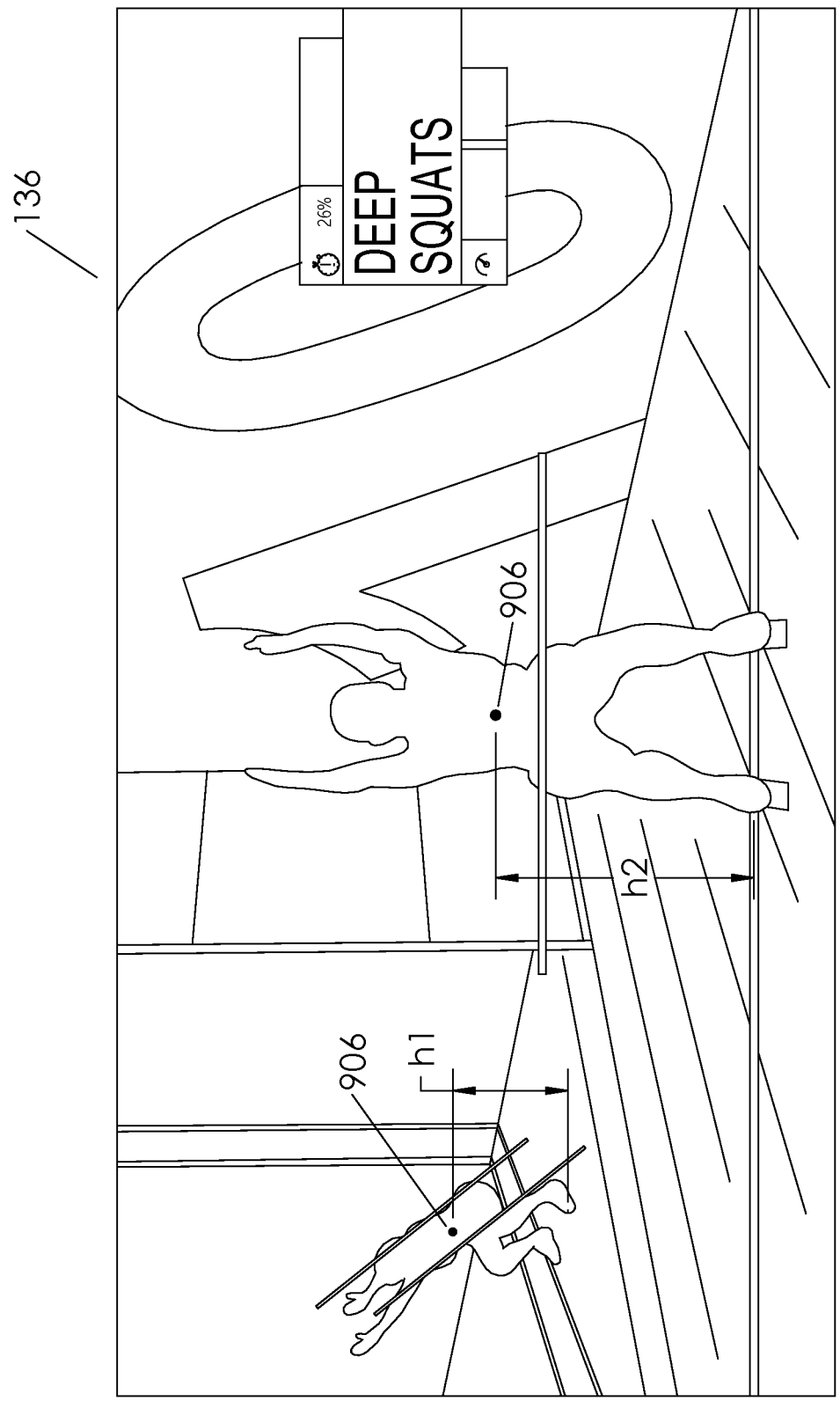

In block 806, various embodiments may involve identifying a change in the location of the center of mass from the first time instant to a second time instant. As discussed above, system 100 may determine locations 904A-D and 906 at one time and at a subsequent time. For example and with reference to FIGS. 10A-B, a user is shown performing a lunge. FIG. 10A corresponds to a first time instant and FIG. 10B corresponds to a second time instant. In FIG. 10A, a location 906 of a user's center of mass is at a height "h1" (designated by 908A) off of the ground. In FIG. 10B, a location 906 of a user's center of mass is at a height "h2" (designated by 908A) off of the ground. One or more components of system 100 may determine a difference between height "h1" and "h2" to determine a change in a location 906 of the center of mass. System 100 may also calculate changes to locations 904A-D of centers of mass for other body parts, or changes to other locations of body parts or body regions of the user. System 100 may also process video of a user taken from different angles, as shown in FIG. 11, to determine locations 904A-D and 906. For example, system 100 may determine height "h1" for location 906 in a perspective view and height "h2" for location 906 in a front view of the user. System 100 may average the different height measurements, or may use one or the other.

With reference again to FIG. 8, in block 808, various embodiments may calculate an energy expenditure estimate for the user due to the change. In an example, the physics concept of potential energy may be used to estimate the amount of work done by the user, and to calculate calories burned based on work.

In an example, one or more components of system 100 may determine changes of a location 906 from one time instant to another to determine an amount of work performed by the user. Potential Energy (PE)=m*g*h, where m=mass of the user (or body part), g=the acceleration due to gravity, and h=height above ground. Work (W)=−ΔPE, where Δ is represents a change in potential energy. Substituting m*g*h, Work (W)=−m*g*Δh. Based on the above example in FIGS. 10A-B, W=−m*g*(h1−h2). System 100 may determine an amount of calories burned as a function of work multiplied by physiology of human efficiency. System 100 may determine the amount of calories burned based on the amount of work and a physiology of human efficiency (PHE) scaling factor. The system 100 may determine the PHE scaling factor as a function of one or more of the user's heart rate, pressure sensor data, and other information input by the user (e.g., age, weight, etc.)

System 100 may keep and/or transmit a running total of calories burned between subsequent time instants and inform the user of a total amount of calories burned up to that point in an exercise session. For example, system 100 may determine a height h of location 906 at a certain frequency (e.g., 2 times per second), and may calculate calories burned based on a difference in calories burned between each determination of height h. The system 100 may also track a total number of calories burned over a predetermined time range covering one or more workouts. A time range may include a week, month, year, cumulative time since a user began working out, or other defined metrics. One or metrics may comprise default values, predefined values, user-selectable values, and/or user-defined values. For example, system 100 may inform the user of how many calories they have burned during a specified time period, such as a day, week, month, and/or year. System 100 may also maintain data on average number of calories burned per workout, average number of calories burned based on a type of workout, a greatest number of calories burned during a single workout or during a predetermined time interval (e.g., month where highest amount of calories were burned), or other types of data.

In another example, system 100 may determine calories burned by movement of a particular body part or by a collection of body parts. For instance, a user may desire to know how many calories were burned by movement of their right leg. Using the above relationship between work and potential energy, and with reference again to FIG. 9, system 100 may monitor changes in the location 904A of the center of mass of the user's right leg (e.g., height 908B) from one time instant to a different time instant to calculate work. System 100 may estimate the mass of the user's right leg based on the user's weight and proportions. System 100 may then determine an amount of calories burned as a function of work multiplied by physiology of human efficiency, as described above. During an exercise session, system 100 may display, such as through display 136, a running total of calories burned attributable to movement of the user's right leg. System 100 may similarly determine calories burned based on locations 904B-D for the other limbs of the user. During an exercise session, system 100 may display a running total of calories burned by a user's entire body, as well by each limb.

System 100 may also permit a user to review an exercise session to determine how many calories were burned at certain times. For example, an exercise may involve performing repetitive motions (e.g., pushups). System 100 may identify each repetition within a set (e.g., each pushup within a set of 10), as well as a number of calories burned during each repetition. Over a set, one or more components of system 100 may identify the repetition where the user burned a highest number of calories as well as a lowest number of calories. In further embodiments, system 100 may estimate an average number of calories. These are merely exemplary statistics and those skilled in the art will readily appreciate that other analysis may be conducted without departing from the scope of this disclosure.

If an exercise session involves different types of exercises, system 100 may rank the exercise types based on the amount of calories burned by type. For example, an exercise session may involve 3 different types of exercises (e.g., pushups, sit-ups, squats). After completing the exercise session, system 100 may determine how many calories were burned by each exercise type (e.g., 10 calories for pushups, 13 calories for sit-ups, and 18 calories for squats), and rank the exercise types based on the number of calories burned (e.g., first squats, second sit-ups, third pushups). In further embodiments, energy expenditure (e.g., a quantity of calories burned) may be ranked as percentage over an ideal value or range for an exercise or routine. For example, if perfectly performing an exercise would burn about 100 calories, a first user who burned 90 calories may be assigned a better ranking than second user who only burned 85 for the same exercise. The users could have different ideal values or ranges, thus the determinations may utilize the percentage of the detected and/or estimated values as a percentage for that user's ideal value. In further embodiments, a user who is closer to 100% of their ideal value may be ranked higher than users who have over 100% of the ideal quantity of calories burned. In this regard, a user who expends more energy than estimated or calculated for an activity (e.g., exercise) may indicate improper movements, inefficiency, increased likelihood of injury, and/or combinations thereof. In certain implementations, the method of FIG. 8 may then end, or may return to any of the preceding blocks and/or other processes.

System 100 may also determine calories expended from pre-recorded videos. For example, a user may upload video of a professional basketball player dunking a basketball to system 100. One or more components of system 100 may process the video to determine locations of a center of mass of the player, or of particular body parts, at various points in time, and determine the amount of calories expended during the physical activity (e.g., by the player during the dunk) using the work-based calorie determination, described above.

CONCLUSION

Providing an activity environment having one or more of the features described herein may provide a user with an immersive experience that will encourage and motivate the user to engage in athletic activities and improve his or her fitness. Users may further communicate through social communities and challenge one another to reach various levels of fitness, and to view their fitness level and activity.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A computer-implemented method comprising:
receiving, by a computer device positioned on a body of a user, first data from a first sensor integrated into an item of apparel worn by the user;
determining, by a processor of the computer device, a location of the computer device on the body of the user, based on the received first data;
receiving, by the computer device, second data from a second sensor integrated within the computer device;
receiving, by the computer device, third sensor data received from a third sensor configured to detect a pressure exerted by the user;
calculating, by the processor, from the second sensor data and the third sensor data, an initial postural assessment of the user;
prompting the user to perform an exercise selected based on the postural assessment and a likelihood of injury to the user;
calculating, by the processor, from the second sensor data and the third sensor data, an angle between a first body part and a second body part of the user, based on the determined location of the computer device on the body of the user;
determining, by the processor, a form of the user, based on the calculated angle;
comparing the determined form of the user to a desired form associated with the exercise;
calculating, by the processor, a completeness modifier based on the comparing the determined form of the user to the desired form; and
calculating, by the processor, an energy expenditure estimate for the user performing the exercise based on a type of the exercise and on the calculated completeness modifier.

2. The method of claim 1, wherein the calculating of the energy expenditure estimate is determined utilizing a metabolic equivalent of task (MET) table for the type of the exercise.

3. The method of claim 1, wherein the energy expenditure estimate is based on a basal metabolic rate of the user.

4. The method of claim 1, wherein the calculating of the energy expenditure estimate applies the following equation:

Calories burned=BMR*(activity modifier)*(completeness modifier), wherein BMR is a Basal Metabolic Rate of the user, and the activity modifier is an adjustment corresponding to the type of the exercise.

5. The method of claim 1, wherein the determining the form of the user is based on processing of video of the user performing the exercise.

6. The method of claim 1, wherein the calculating of the angle comprises:
processing of infrared data received from the first sensor and the second sensor.

7. The method of claim 1, wherein the comparing the determined form of the user to the desired form comprises comparison of the calculated angle to one or more threshold angle values.

8. The method of claim 1, wherein the calculating of the angle comprises:
processing of acceleration data received from the first sensor and the second sensor.

9. The method of claim 1, wherein the calculating of the energy expenditure estimate comprises increasing or decreasing the estimate based on the calculated completeness modifier.

10. A tangible, non-transitory computer-readable medium comprising computer-executable instructions that, when executed, perform a method comprising:
receiving, by a computer device positioned on a body of a user, first data from a first electronic sensor integrated into an item of apparel worn by the user;
determining, a location of the computer device on the body of the user, based on the received first data;
receiving by the computer device, second data from a pressure sensor;
calculating, from the received second data, an initial postural assessment of the user;

prompting the user to perform an exercise selected based on the postural assessment and a likelihood of injury to the user;

calculating, from the received second data, an angle between a first body part and a second body part of a user;

determining a form of the user, based on the calculated angle;

comparing the determined form of the user to a desired form associated with the exercise;

calculating a completeness modifier based on the comparing the determined form of the user to the desired form; and calculating an energy expenditure estimate for the user performing the exercise based on a type of the exercise and on the calculated completeness modifier.

11. The non-transitory computer-readable medium of claim 10, wherein the energy expenditure estimate is based on a basal metabolic rate of the user.

12. The non-transitory computer-readable medium of claim 10, wherein the calculating of the energy expenditure estimate applies the following equation:

$$\text{Calories burned} = \text{BMR} * (\text{activity modifier}) * (\text{completeness modifier}),$$

wherein BMR is a Basal Metabolic Rate of the user, and the activity modifier is an adjustment corresponding to the type of the exercise.

13. The non-transitory computer-readable medium of claim 10, wherein the determining the form of the user is based on processing of video of the user performing the exercise or based on processing of an infrared reflection of the user.

14. The non-transitory computer-readable medium of claim 10, wherein the calculating of the energy expenditure estimate comprises increasing or decreasing the estimate based on the calculated completeness modifier.

15. An apparatus configured to be worn on a body of a user comprising:
at least one processor; and
at least one memory storing instructions that, when executed, cause the apparatus at least to perform:
receiving first data from a user-worn electronic sensor integrated into an item of apparel worn by the user;
calculating, from the first data, a location of the apparatus on the body of the user;
receiving second data from a sensor integrated within the apparatus;
receiving third data from a pressure sensor;
calculating, from the second sensor data and the third sensor data, an initial postural assessment of the user;
prompting a user to perform an exercise selected based on the postural assessment and a likelihood of injury to the user;
calculating, from the second sensor data and the third sensor data, an angle between a first body part and a second body part of the user;
determining a form of the user, based on the calculated angle;
comparing the determined form of the user to a desired form associated with the exercise;
calculating, by the processor, a completeness modifier based on the comparing the determined form of the user to the desired form; and
calculating an energy expenditure estimate for the user performing the exercise based on a type of the exercise and on the calculated completeness modifier.

16. The apparatus of claim 15, wherein the energy expenditure estimate is based on a basal metabolic rate of the user.

17. The apparatus of claim 15, wherein the calculating of the energy expenditure estimate applies the following equation:

$$\text{Calories burned} = \text{BMR} * (\text{activity modifier}) * (\text{completeness modifier}),$$

wherein BMR is a Basal Metabolic Rate of the user, and the activity modifier is an adjustment corresponding to the type of the exercise.

18. The apparatus of claim 15, wherein the determining the form of the user is based on processing of video of the user performing the exercise.

19. The apparatus of claim 15, wherein the determining the form of the user is based on processing of an infrared reflection of the user.

20. The apparatus of claim 15, wherein the calculating of the energy expenditure estimate comprises increasing or decreasing the estimate based on the calculated completeness modifier.

* * * * *